(12) United States Patent
Peck et al.

(10) Patent No.: US 8,235,209 B2
(45) Date of Patent: Aug. 7, 2012

(54) MEDICAL DEVICE PACKAGING AND METHODS FOR PREPARING AND PACKAGING MEDICAL DEVICES

(75) Inventors: James M. Peck, Maple Grove, MN (US); Maan-Shii Wu, Mendota Heights, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/854,607

(22) Filed: Aug. 11, 2010

(65) Prior Publication Data

US 2012/0037525 A1  Feb. 16, 2012

(51) Int. Cl.
*B65D 83/10* (2006.01)
*B65D 85/00* (2006.01)
*A61L 2/20* (2006.01)

(52) U.S. Cl. ........... 206/364; 206/439; 422/28; 422/292
(58) Field of Classification Search .................. 206/363, 206/364, 438, 439; 604/174–175; 422/26–28, 422/292
See application file for complete search history.

(56) References Cited

U.S. PATENT DOCUMENTS

| | | | |
|---|---|---|---|
| 3,754,700 A | 8/1973 | Bonk | |
| 3,851,814 A * | 12/1974 | Stage | 206/439 |
| 3,926,311 A * | 12/1975 | Laske | 206/439 |
| 3,942,634 A | 3/1976 | Gandi et al. | |
| 4,154,342 A * | 5/1979 | Wallace | 206/439 |
| 4,216,860 A | 8/1980 | Heimann | |
| 4,730,726 A | 3/1988 | Holzwarth | |
| 4,861,632 A | 8/1989 | Caggiano | |
| 4,941,308 A | 7/1990 | Grabenkort et al. | |
| 5,217,114 A | 6/1993 | Gadberry et al. | |
| 5,577,368 A | 11/1996 | Hamilton et al. | |
| 5,590,778 A | 1/1997 | Dutchik | |
| 5,620,656 A | 4/1997 | Wensky et al. | |
| 5,681,322 A | 10/1997 | Hartigan, Jr. | |
| 5,690,623 A | 11/1997 | Lenz | |
| 5,730,150 A | 3/1998 | Peppel et al. | |
| 5,848,691 A | 12/1998 | Morris et al. | |
| 5,874,045 A | 2/1999 | Chisum | |
| 5,928,516 A | 7/1999 | Hopkins et al. | |
| 5,935,501 A | 8/1999 | Andrews et al. | |
| 6,065,597 A | 5/2000 | Pettersson et al. | |

(Continued)

FOREIGN PATENT DOCUMENTS

EP  0492399 A2  7/1992

(Continued)

OTHER PUBLICATIONS

"Tekni-Films Instroduces TEKNIFLEX® Modified Atmosphere Blister (MAB) Package," Article from http://www.tekni-films.com website, Mar. 29, 2006.

*Primary Examiner* — Bryon Gehman
(74) *Attorney, Agent, or Firm* — Seager, Tufte & Wickhem, LLC (57) ABSTRACT

Medical device packaging, medical device packaging assemblies, and methods for preparing and packaging medical devices. An example medical device packaging assembly may include a pouch having a pocket formed therein. A carrier tube may be disposed in the pocket. The carrier tube may have a plurality of apertures formed therein. A medical device may be disposed within the carrier tube.

20 Claims, 8 Drawing Sheets

U.S. PATENT DOCUMENTS

| | | |
|---|---|---|
| 6,174,934 B1 | 1/2001 | Sun |
| 6,312,646 B2 | 11/2001 | Kowanko |
| 6,423,226 B1 | 7/2002 | Hopkins et al. |
| 6,585,702 B1 | 7/2003 | Brunel |
| 6,871,740 B1 * | 3/2005 | Cao ............................ 206/364 |
| 6,875,400 B2 | 4/2005 | Speer |
| 7,000,770 B2 | 2/2006 | Clarke |
| 7,040,485 B2 | 5/2006 | Gupta |
| 7,108,682 B2 | 9/2006 | Duffy et al. |
| 7,178,555 B2 | 2/2007 | Engel |
| 7,211,308 B2 | 5/2007 | Rhee |
| 7,234,597 B2 * | 6/2007 | Rowe et al. ................... 206/438 |
| 7,261,205 B2 | 8/2007 | Cervantes |
| 7,303,734 B2 | 12/2007 | Moriyama |
| 7,337,593 B2 | 3/2008 | Blum |
| 7,353,946 B2 * | 4/2008 | Cervantes ..................... 206/364 |
| 7,631,760 B2 | 12/2009 | Guelzow et al. |
| 7,694,810 B1 * | 4/2010 | Barry et al. ................... 206/364 |
| 7,694,813 B2 * | 4/2010 | Shalaby ........................ 206/439 |
| 7,762,044 B2 * | 7/2010 | Clarke et al. .................... 53/425 |
| 7,776,003 B2 * | 8/2010 | Zauner ........................ 604/175 |
| 7,909,249 B2 * | 3/2011 | Bagozzi et al. ................ 235/385 |
| 2002/0015673 A1 | 2/2002 | Moriyama |
| 2003/0008152 A1 | 1/2003 | Tsai |
| 2003/0178329 A1 | 9/2003 | Furukawa |
| 2004/0155053 A1 | 8/2004 | Sanchez |
| 2004/0187438 A1 | 9/2004 | Clarke |
| 2004/0243214 A1 | 12/2004 | Farrell |
| 2005/0109648 A1 | 5/2005 | Kerzman et al. |
| 2005/0143803 A1 | 6/2005 | Watson |
| 2005/0199521 A1 | 9/2005 | Givens |
| 2005/0218022 A1 | 10/2005 | Cervantes |
| 2005/0278012 A1 | 12/2005 | Vonderwalde |
| 2006/0016708 A1 | 1/2006 | Ingraham |
| 2006/0086254 A1 | 4/2006 | Fudge et al. |
| 2006/0260967 A1 | 11/2006 | Clarke et al. |
| 2007/0014951 A1 | 1/2007 | Soerensen et al. |
| 2007/0084144 A1 | 4/2007 | Labrecque et al. |
| 2007/0092167 A1 | 4/2007 | Tilman et al. |
| 2009/0269444 A1 | 10/2009 | Thomas, Jr. |
| 2009/0314676 A1 | 12/2009 | Peck et al. |
| 2011/0079525 A1 | 4/2011 | Peck et al. |

FOREIGN PATENT DOCUMENTS

| | | |
|---|---|---|
| EP | 0629415 A1 | 12/1994 |
| EP | 0782868 A1 | 7/1997 |
| EP | 0944474 B1 | 10/2002 |
| WO | 9903754 A1 | 1/1999 |
| WO | 2004066876 A1 | 8/2004 |
| WO | 2004071308 A1 | 8/2004 |
| WO | 2005058586 A2 | 6/2005 |
| WO | 2005058586 A3 | 5/2007 |

\* cited by examiner

MEDICAL DEVICE PACKAGING AND METHODS FOR PREPARING AND PACKAGING MEDICAL DEVICES

TECHNICAL FIELD

The present invention pertains to medical devices, medical device packaging, and methods for preparing and packaging medical devices. More particularly, the present invention pertains to carrier tubes for use in medical device packaging.

BACKGROUND

A wide variety of intracorporeal medical devices have been developed for medical use, for example, intravascular use. Some of these devices include guidewires, catheters, and the like. These devices are manufactured, packaged, and/or prepared by any one of a variety of methods. Of the known medical devices and methods, each has certain advantages and disadvantages. There is an ongoing need to provide alternative medical devices as well as alternative methods for manufacturing, packaging, and/or preparing medical devices.

BRIEF SUMMARY

Embodiments of the present disclosure provide design, material, and use alternatives for medical device packaging and packaging assemblies, as well as methods for preparing and packaging medical devices. An example medical device packaging assembly includes a pouch having a pocket formed therein. A carrier tube is disposed in the pocket. The carrier tube has a plurality of apertures formed therein. A medical device is disposed within the carrier tube.

An example method of preparing a medical device includes providing a carrier tube, disposing a medical device within the carrier tube to define a medical device assembly, disposing the medical device assembly within a packaging pouch, and exposing the medical device assembly to an alternative atmosphere. The carrier tube has a tube wall with a plurality of apertures formed therein.

An example time-efficient method for ethylene oxide sterilization of medical devices includes providing a carrier tube, disposing a medical device within the carrier tube to define a medical device assembly, disposing the medical device assembly within a packaging pouch, and exposing the medical device assembly to ethylene oxide for less than about 12 hours. The carrier tube has a tube wall with a plurality of apertures formed therein.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

Embodiments of the present disclosure may be more completely understood in consideration of the following detailed description in connection with the accompanying drawings, in which.

While embodiments described herein are is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

For obvious reasons, medical devices are typically sterilized or otherwise prepared for use prior to sale. In order to preserve sterility, medical devices are usually contained within appropriate packaging that allows the sterile medical devices to be shipped to and stored by the purchaser. For example, prior to sale, medical devices such as catheters are typically sterilized and packaged. When suitably prepared, the catheters can be transported to an appropriate medical setting where they can be stored until needed for use.

Because devices like catheters may be susceptible to damage when shipped and/or stored, catheters may be disposed within a tube or shell often termed a carrier tube. The carrier tube affords the catheter some level of protection during the shipping/storage phase as well as, for example, during preparation prior to a clinical intervention. Other desirable benefits may also be achieved through the use of a carrier tube. It can be appreciated that in order to maintain the sterility of the catheter, the catheter may be disposed within the carrier tube prior to sterilization and can then be left within the packaging in order to serve its intended purpose.

Due to the relative fragility of the medical devices and the potential that the materials utilized in the manufacturing of the medical device may be adversely affected by the heat associated with traditional steam sterilization or autoclaving, other sterilization protocols are typically utilized for such devices. For example, a number of different medical devices are often sterilized using ethylene oxide sterilization techniques. Ethylene oxide sterilization techniques generally involve the exposure of the device to be sterilized to a suitable ethylene oxide environment. A number of additional conditions may also be needed such as particular relative humidity conditions, temperature, etc. in order to achieve the desired biological indication of sterility.

Because the medical devices may be packaged within a carrier tube, the time that the device and the carrier tube needs to be exposed to the ethylene oxide may be generally long. For example, the exposure time for a typical medical device to ethylene oxide may be greater than 12 hours. This may be due to the fact that in order for the sterilization medium (e.g., ethylene oxide) to reach the entire length of the medical device, the sterilization medium enters the carrier tube at one of the two ends and then diffuses to and throughout the full length of the medical device. This length may be relatively long, such as 100 to 500 centimeters (cm) or so. In addition, because diffusion may be a relatively slow process, the time required for the sterilization medium to effectively reach the entire medical device may be reasonably long. It can be appreciated that the total time required to suitably sterilize a medical device may be significant, thus consuming significant resources. For example, a typical ethylene oxide sterilization process may take in excess of 12 hours, or about 12 to 48 hours or more.

Disclosed herein are a number of medical device packages and/or packaging components, methods for packaging and/or preparing a medical device for sale, and methods for improving the shelf life of medical devices. In at least some embodiments, the packages, packaging components, and methods may allow for or otherwise include preparation steps that are shorter than typical preparation methods, thereby reducing the resources utilized. Other features and benefits are also disclosed, as discussed herein.

Figure 1:
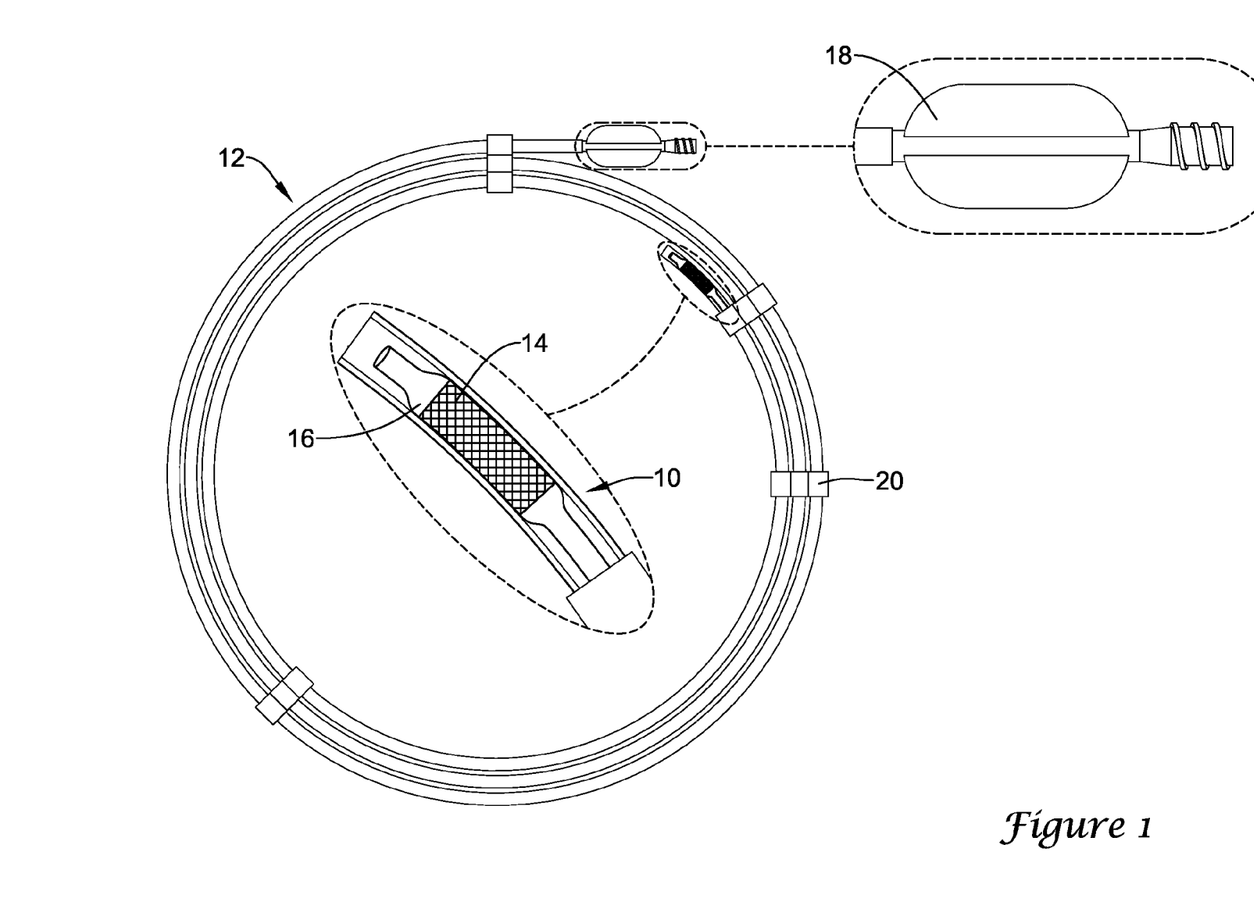
FIG. 1 is a side view of an example medical device disposed within an example carrier tube.

FIG. 1 illustrates an example medical device 10 disposed within a carrier tube 12. In this example, medical device 10 may include a catheter for delivery of an endoprosthesis. For example, medical device 10 may include an endoprosthesis or stent 14 attached thereto. In some embodiments, stent 14 is disposed on a balloon 16, which may be used to expand stent 14. In other embodiments, stent 14 is a self-expanding stent and, as such, medical device 10 may be a catheter suitable for delivery thereof. In either embodiment, stent 14 may be a bare metal stent or may include one or more substances associated therewith such as pharmaceuticals or the like (e.g., stent 14 may be a drug-eluting stent). Medical device 10 may also include a proximal hub 18. It can be appreciated that medical device 10 may differ vastly in form and can include any other suitable medical devices including catheters, guidewires, or the like.

Carrier tube 12 may generally be configured to hold medical device 10 in a suitable configuration. In at least some embodiments, carrier tube 12 may be arranged or otherwise configured as a coil that allows medical device 10, which may have a reasonably long length, to be held in a compact configuration. The individual windings of the coil may be secured together by one or more clips 20 as is typical in the art. Other configurations for carrier tube 12 include configurations suitable for holding other medical devices.

Figure 2:
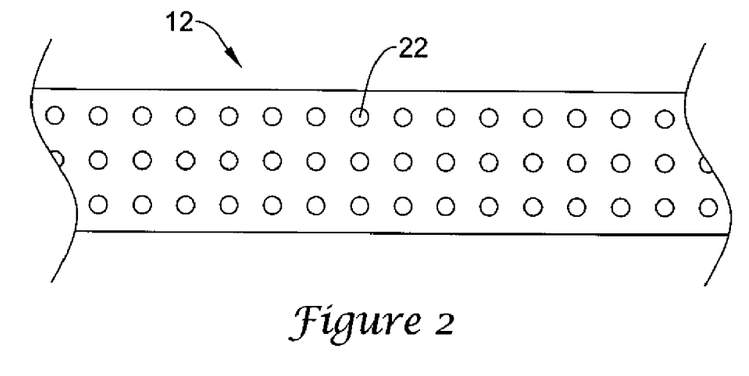
FIG. 2 is a side view of a portion of an example carrier tube.

As indicated herein, medical devices such as medical device 10 may need to be prepared and/or packaged prior to sale or use. Such preparation may include sterilization such as sterilization via an ethylene oxide sterilization technique. As illustrated in FIG. 2, in order to decrease the amount of preparation time relative to other carrier tubes, carrier tube 12 may be configured with a plurality of openings or apertures 22. In general, apertures 22 may be designed to allow an external (or alternative) atmosphere or other condition to have more rapid access to medical device 10 for sterilization, preparation, or any other desired purpose, as compared to a carrier tube without apertures. For example, apertures 22 may allow medical device 10 to be exposed to the alternative atmosphere for less than about 12 hours, less than about 8 hours, or less than about 4 hours, for example, to achieve sterilization (e.g., substantially 100% biological kill) or to otherwise be prepared in the desired manner.

The number, configuration, and arrangement, of apertures 22 may vary. In some embodiments, carrier tube 12 may include about 3 to 1000 apertures 22, about 10 to 500 apertures 22, about 25 to 200 apertures 22, or about 50 to 150 apertures. In one embodiment, carrier tube 12 may include about 100 apertures. It can be appreciated that the number of apertures 22 may vary.

Figure 3:
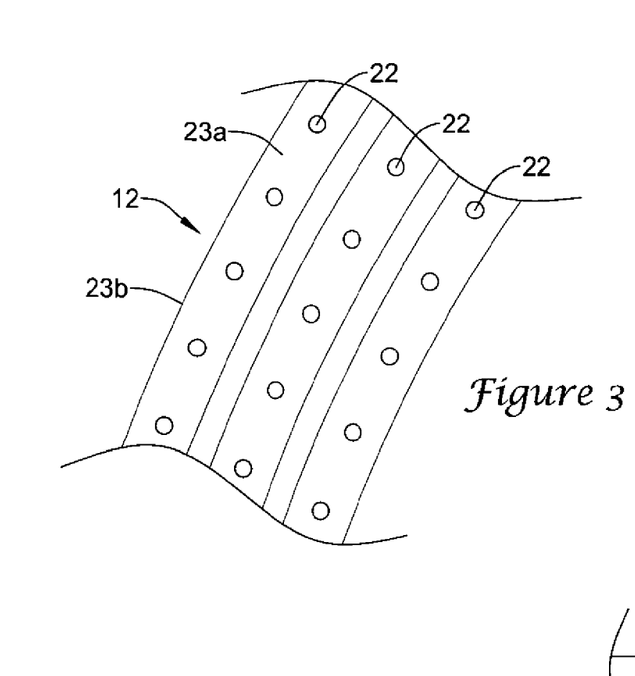
FIG. 3 is a top view of a portion of an example carrier tube illustrated in FIG. 2 in a coil-like configuration.

Apertures 22 may be disposed in many suitable arrangement. For example, FIG. 3 illustrates a portion of carrier tube 12 with an arrangement of apertures 22 that include apertures generally disposed along an exposed or "top" surface 23a as opposed to a side or peripheral surface 23b. In this arrangement, apertures 22 generally are positioned so that each aperture 22 can be exposed to the appropriate alternative atmosphere or environment while carrier tube 12 is in a coiled configuration. Conversely, if apertures 22 were positioned along surfaces 23b, these apertures 22 may be covered by subsequent windings or coils of carrier tube 12, thus obscuring access to apertures 22. It can be appreciated that other arrangements are also contemplated for apertures 22 including those that may include apertures 22 disposed along other suitable wall surfaces of carrier tube 12.

Figure 2A:
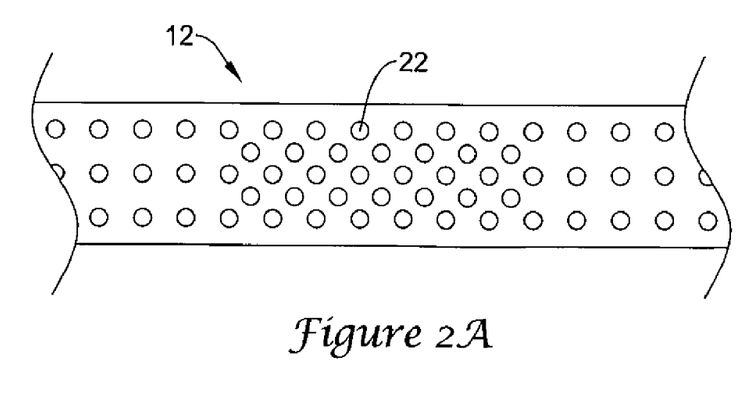
FIG. 2A is a side view of a portion of an example carrier tube.

The pattern or density of apertures 22 may also vary. For example, it may be desirable for apertures 22 to be arranged in a substantially constant or "regular" pattern having a substantially constant density. Alternatively, variations in the pattern and/or density are also contemplated. For example, it may be desirable for the density of apertures 22 to be generally greatest at positions furthest away from the ends of carrier tube 12 (e.g., as shown in FIG. 2A). Thus, the central or middle portions of carrier tube 12 may have a greater density of apertures 22 than the ends. Other arrangements are contemplated including variations where the density of apertures 22 is variable along the length of carrier tube 12. Indeed, in some embodiment, portions of carrier tube 12 may lack apertures 22 altogether whereas other portions may include a suitable number or density of apertures 22.

Figure 4:
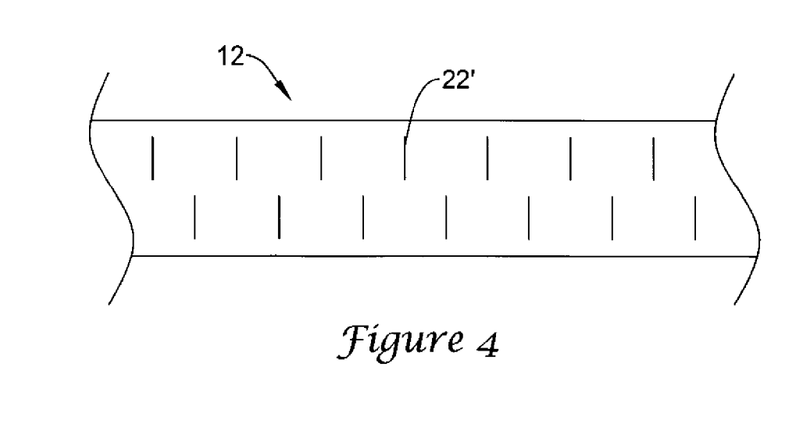
FIG. 4 is a side view of a portion of another example carrier tube.

The shape of apertures 22 may also vary. For example, apertures 22 are illustrated as being round holes or apertures in FIGS. 2-3. This, however is not intended to be limiting as other suitable shapes may be utilized. For example, FIG. 4 illustrates another arrangement where apertures 22' are rectangular in shape or otherwise take the form of "slots". It can be appreciated that the precise shape of apertures 22/22' may vary and at least some embodiments of carrier tube 12 include apertures 22 of one or more different shapes or configurations. This may include other suitable geometric shapes (e.g., circular, oval, triangular, square, rectangular, pentagonal, hexagonal, etc.), other shapes (e.g., "L" shaped, "U" shaped, tear drop shaped, pill shaped, etc.), or other suitable shapes.

Carrier tube 12 may generally be formed of a polymer material. Some examples of suitable polymers include polytetrafluoroethylene (PTFE), ethylene tetrafluoroethylene (ETFE), fluorinated ethylene propylene (FEP), polyoxymethylene (POM), for example, DELRIN® available from DuPont), polyether block ester, polyurethane, polypropylene (PP), polyvinylchloride (PVC), polyether-ester (for example, ARNITEL® available from DSM Engineering Plastics), ether or ester based copolymers (for example, butylene/poly (alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene (for example MARLEX® high-density polyethylene), low-density polyethylene (for example MARLEX® low-density polyethylene), linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). Carrier tube 12 may also include other materials such as metals, metal alloys, or the like.

Carrier tube 12 may be formed in a suitable manner. For example, carrier tube 12 may be formed via an extrusion process. Alternatively, carrier tube 12 may be formed via molding or other suitable process. In some embodiments, apertures 22 may be formed in carrier tube 12 by cutting, drilling, laser cutting, etching, scoring, or other suitable manners. Forming apertures 22 may generally occur after carrier tube 12 is formed. However, this is not intended to be limiting, as processes are contemplated where apertures 22 are defined in carrier tube 12 as part of the process of manufacturing carrier tube 12.

Figure 5:
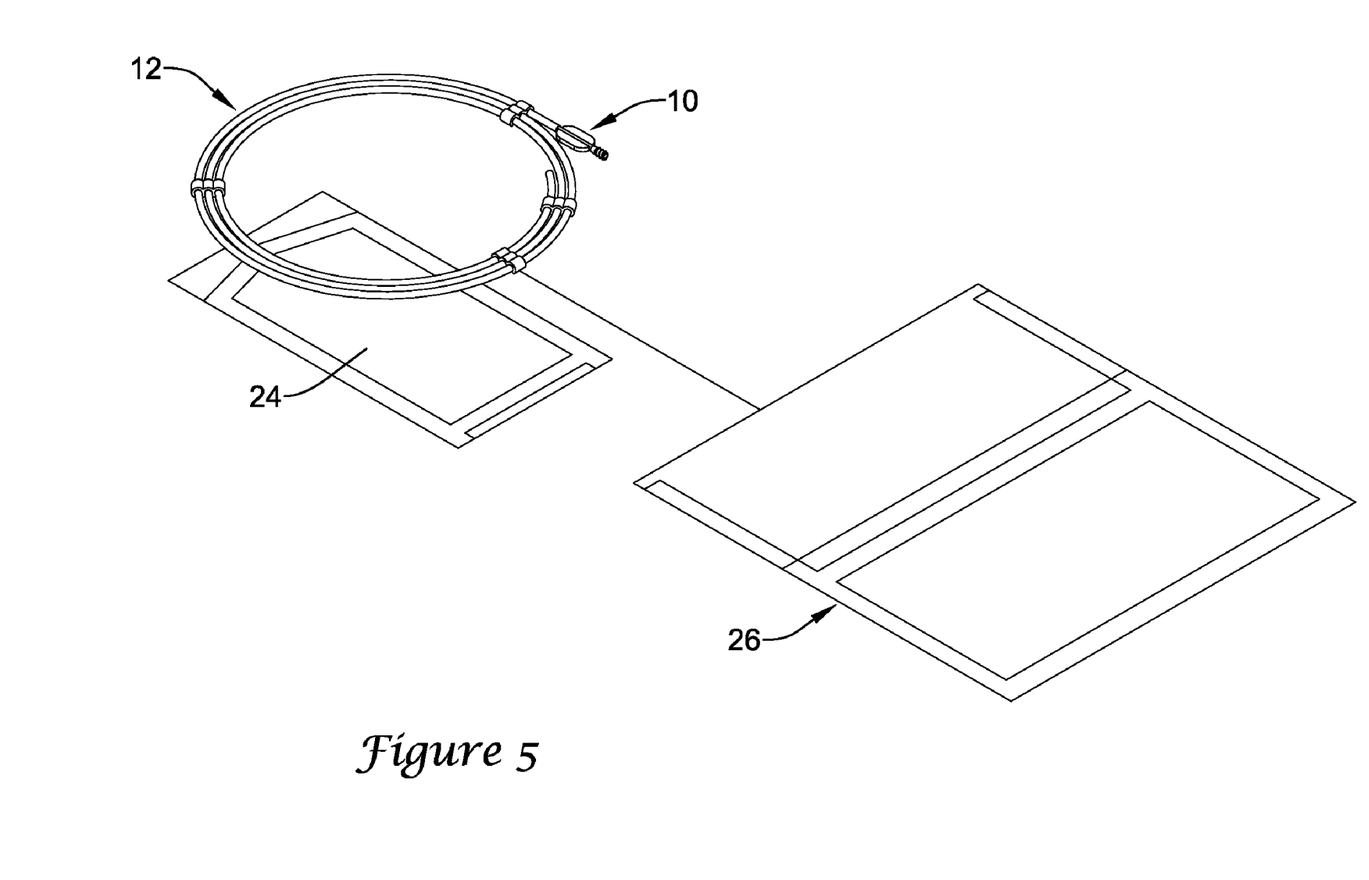
FIG. 5 is an exploded view of an example medical device packaging assembly.
Figure 6:
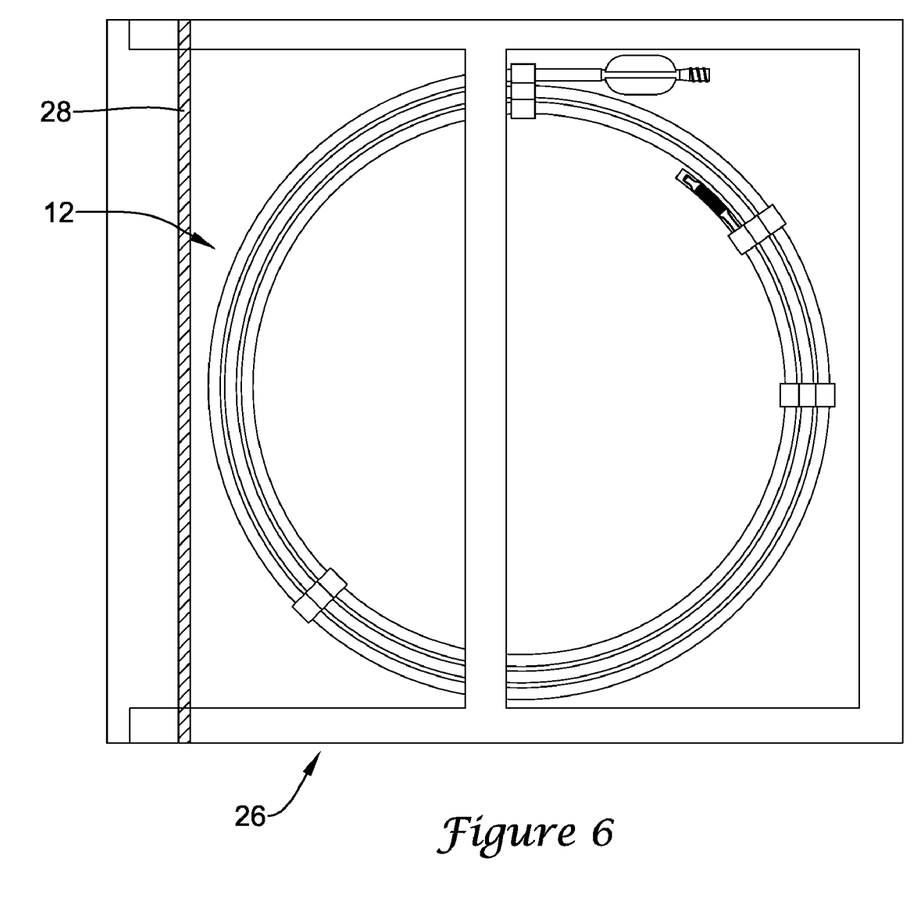
FIG. 6 is a top view of an example medical device packaging assembly.

FIG. 5 is an exploded view of an example medical device packaging assembly. Here it can be seen that carrier tube 12 (having medical device 10 disposed therein) may be disposed on or adjacent a base 24 and then be disposed in a packaging pouch 26. In some embodiments, base 24 may be an accessory pouch (e.g., a kit accessory pouch). Packaging pouch 26 (e.g., which may take the form of a standard pouch or header bag) may be a relatively rigid structure or portions of all of pouch 26 may be flexible. Once so disposed, for example as illustrated in FIG. 6, carrier tube 12 can be subjected to the desired alternative atmosphere. This may include exposure to ethylene oxide (e.g., for sterilization), nitrogen, oxygen, water (e.g., moisture, humidity, etc.), argon or another inert atmosphere, other atmospheres, or the like. Exposure may include one or more cycles of exposure. If multiple cycles are desired, the cycles may have a vacuum exposure between cycles. Once the number of exposures is complete, pouch 26 may be sealed (e.g., at any one of a wide range of pressures) to form a seal 28.

Figure 7:
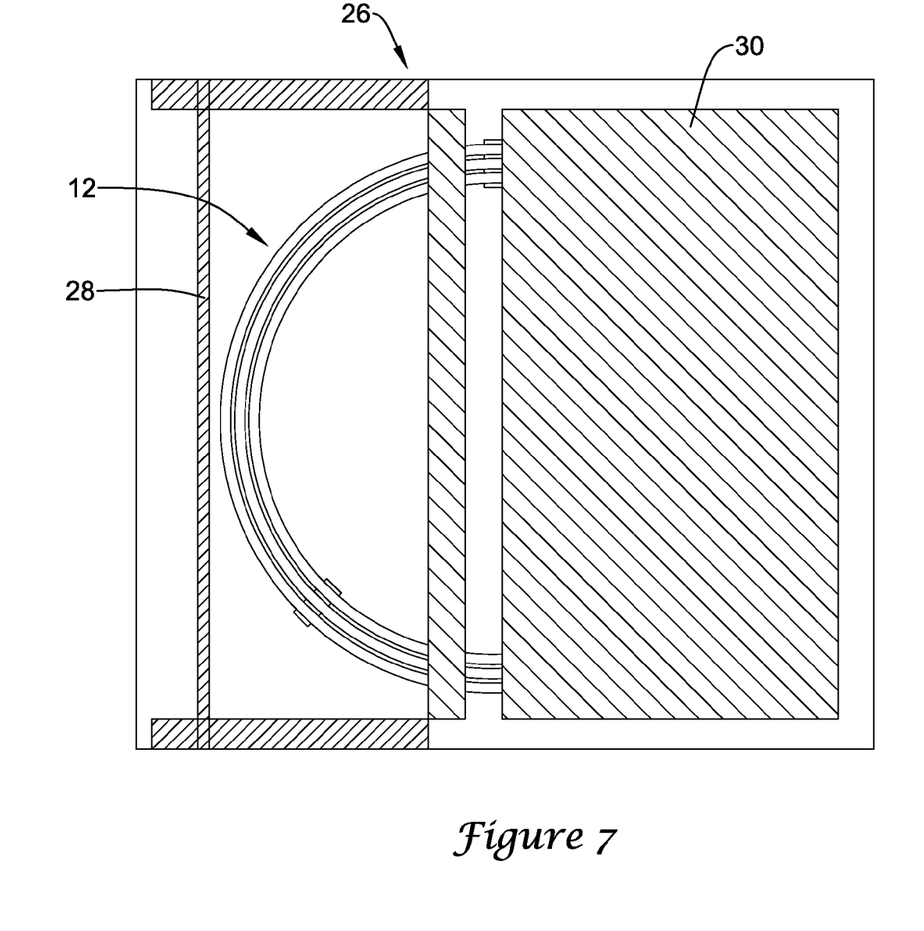
FIG. 7 is a bottom view of an example medical device packaging assembly.

Packaging pouch 26 may include one or more additional features or structures associated therewith. For example, in some embodiments pouch 26 may have a breathable layer, for example breathable layer 30 disposed along a bottom of pouch 26 as shown in FIG. 7, that allows for some substances (e.g., moisture, air, etc.) to escape pouch 26. Layer 30 may include a suitable material such as, for example, high-density polyethylene (e.g., TYVEK®, commercially available from DuPont), a porous material, coated paper, combinations thereof, and the like, or any other suitable material. Layer 30 may be disposed along any portion of the surface area (and may take any shape along the surface area) of pouch 26. In addition, packaging pouch 26 may include other sachet or packet structures such as the inclusion of a desiccant or oxygen scavenger material that may help manage moisture or oxygen within pouch 26 and keep the moisture at a desired level.

Because carrier tube 12 includes apertures, the total time for exposure to the alternative atmosphere can be reduced (relative to the time necessary when a carrier tube lacking apertures is utilized). For example, with reference to an ethylene oxide sterilization protocol, ethylene oxide can reach the interior of carrier tube 12 at an increased rate via apertures 22 than that of a carrier tube lacking apertures. Accordingly, the total length of medical device 10 can be subjected to ethylene oxide in a shorter time frame (e.g., a shorter time frame as compared to sterilization techniques that use a carrier tube that lacks apertures). This may be beneficial for a number of reasons. For example, faster exposure (and, analogously, faster removal of the ethylene oxide) shortens the packaging process time (relative to carrier tubes lacking apertures), which can significantly impact the resources required for sterilization. Thus, the sterilization rate can be increased through the use of carrier tube 12. Other benefits may also result from the use of carrier tube 12 including, for example, quicker vacuum packaging, quicker and/or more efficient removal of deleterious materials (e.g., gases) from packaging pouch 26, improved coiling speed, allowing for the use of fewer clips 20, less resistance to irradiation cycles, etc. These are just examples.

Furthermore, exposure to an alternative atmosphere may negatively impact one or more qualities of medical device 10. For example, if medical device 10 includes a drug-eluting stent, exposure of ethylene oxide and/or humidity associated with the ethylene oxide sterilization process may cause the coating on the stent to swell or be otherwise altered. Consequently, the life cycle of the drug coating may be shortened due to exposure to ethylene oxide and/or humidity. This affect on the drug coating, ultimately, can be reflected on the shelf life of a drug-eluting stent. By reducing the time that a drug-eluting stent is exposed to ethylene oxide and/or humidity (e.g., by use of a desiccant), it may be possible to significantly reduce the amount of swelling and/or alteration of the drug coating or other moisture-sensitive coatings, which can significantly increase the shelf life of drug-eluting stents and, thus, medical devices bearing such stents. Other benefits may also be realized.

In at least some other embodiments, the general concept of adding apertures to carrier tube 12 can be applied to other structures of packaging pouch 26. For example, some packages may include a plurality of pouches (e.g., a secondary pouch disposed within a primary or high-barrier pouch). In these embodiments, the secondary pouch may include a plurality of apertures that may allow for quicker ingress/egress of gases as well as other desirable benefits.

EXAMPLES

The following example serves to exemplify some illustrative embodiments, and are not meant to be limiting.

Example 1

A carrier tube was prepared with 100 apertures along the length thereof. The carrier tube was disposed in an example packaging pouch and exposed to vacuum, nitrogen flush, vacuum, nitrogen flush, vacuum, and nitrogen flush (e.g., 3 nitrogen flush cycles interspersed with vacuum). The total quantities of oxygen and water within the packaging pouch (e.g., which may also be termed the package headspace) were monitored.

Nitrogen flushing will flush out oxygen and moisture initially present in the package headspace (and do so more efficiently than within the carrier tube). Once the package is sealed, it is assumed that the concentration of oxygen and moisture is higher within the carrier tube than in the package headspace (the latter being nearly zero). Both oxygen and moisture inside the carrier tube will then begin to migrate out into the package headspace, creating an equilibrium with the entire package.

The quantities of oxygen and water within the packaging pouch was measured over 1,440 hours in a packaging pouch with either a carrier tube lacking apertures (e.g., the "standard" carrier tube) or a carrier tube with apertures (e.g., the "holed" carrier tube). The amount of oxygen detected in the packaging pouch over time is shown graphically in FIG. 8 and the amount of water detected in the packaging pouch over time is shown graphically in FIG. 9. These figures show that in sealed packages, the amount of oxygen and water detected in the package headspace, which is assumed to equate with the amount of oxygen or water that has diffused from inside the carrier tube into the package headspace, initially increases. Eventually, the headspace concentration levels off and reaches an equilibrium with that inside the carrier tube.

Figure 8:
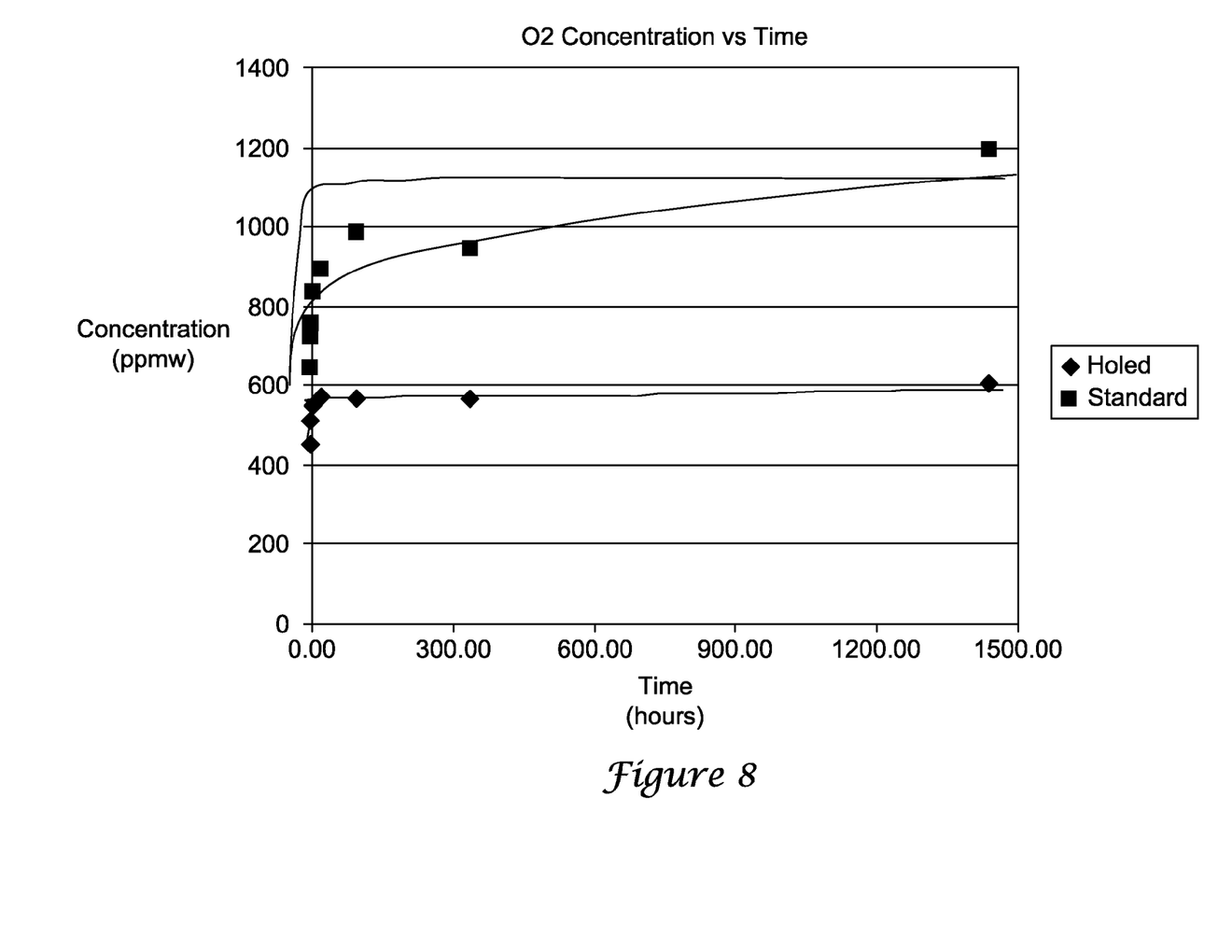
FIG. 8 is graph showing the amount of oxygen detected in a packaging pouch over time for an example carrier tube having apertures formed therein and a control carrier tube lacking apertures.
Figure 9:
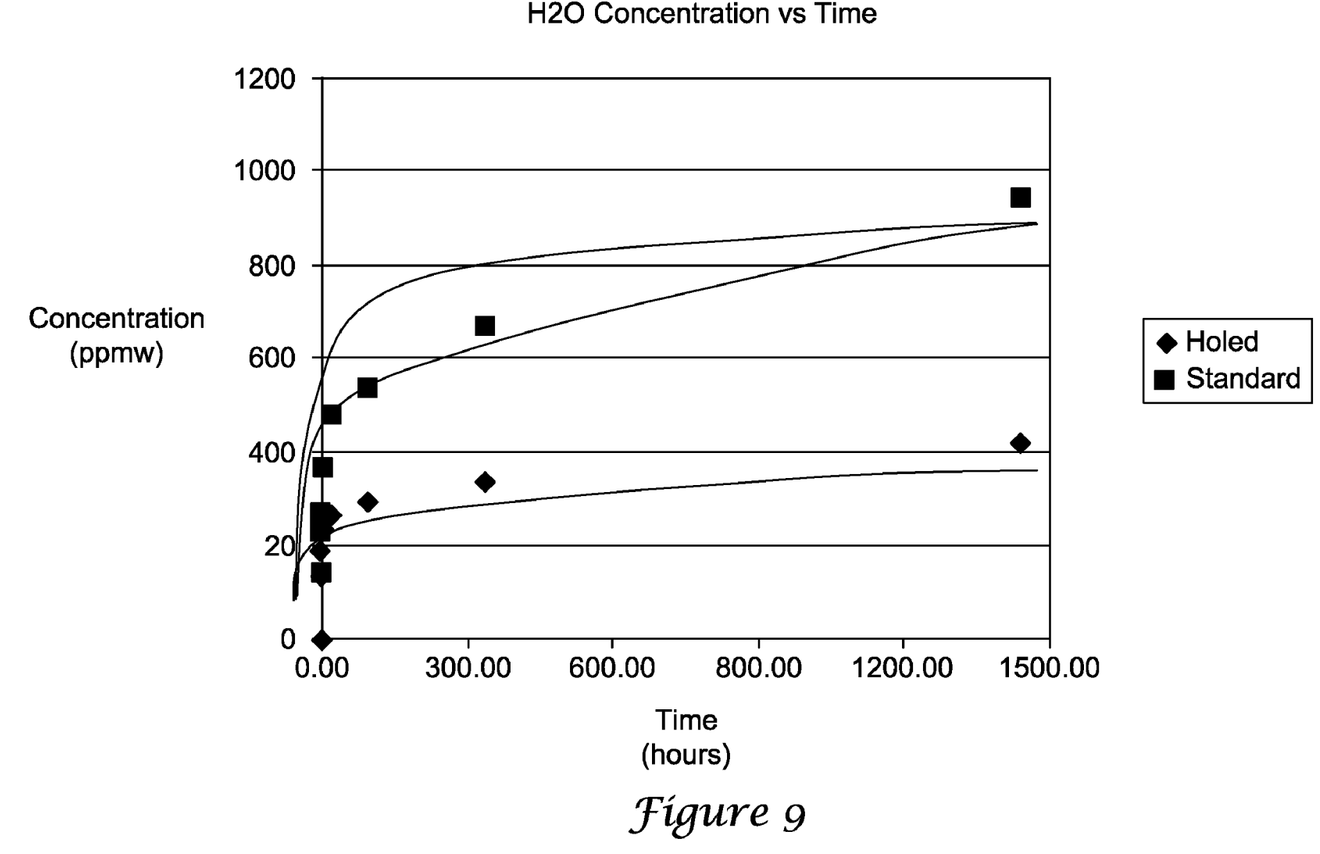
FIG. 9 is graph showing the amount of water detected in a packaging pouch over time for an example carrier tube having apertures formed therein and a control carrier tube lacking apertures.

FIGS. 8 and 9 also show that a carrier tube with apertures allows gas (e.g., oxygen and water) to diffuse more quickly and reach equilibrium earlier than a carrier tube lacking the apertures. For example, it can be seen in these figures that the amount of time to reach this equilibrium is much faster in the packaging pouch that includes the carrier tube with apertures. Indeed, in the carrier tube without apertures, the concentration of oxygen and water appears to still be increasing within the packaging headspace after 1,440 hours.

Because the initial headspace concentration of oxygen and water was different for the carrier tube with apertures than for the carrier tube lacking apertures, FIGS. 8 and 9 also include a third line, positioned directly above the line drawn for the standard carrier tube, which represents the predicted curve that would result for a carrier tube with apertures under the same starting conditions (e.g., starting oxygen and water headspace concentrations). This curve further illustrates the gap between the diffusion efficiency when a carrier tube with apertures is utilized as compared to a carrier tube lacking apertures.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A medical device packaging assembly, comprising:
   a pouch having a pocket formed therein;
   a carrier tube disposed in the pocket, the carrier tube having a proximal end with a proximal opening, a distal end with a distal opening, and a tube body extending between the proximal end and the distal end;
   wherein a plurality of apertures are formed in the tube body, and wherein the apertures are arranged so as to define a density along the length of the tube body and the density of the apertures varies along the length of the tube body; and
   a medical device disposed within the carrier tube.

2. The assembly of claim 1, wherein the carrier tube is configured to improve the rate of ethylene oxide sterilization of the medical device.

3. The assembly of claim 1, wherein the carrier tube is configured to improve the shelf life of the medical device.

4. The assembly of claim 1, wherein the medical device includes a catheter.

5. The assembly of claim 1, wherein the medical device includes a guidewire.

6. The assembly of claim 1, wherein the medical device includes a stent.

7. The assembly of claim 6, wherein the medical device includes a drug-eluting stent.

8. The assembly of claim 6, wherein the medical device includes a stent delivery system.

9. A method of preparing a medical device, the method comprising:
   providing a carrier tube, wherein the carrier tube has a proximal end, a distal end, and a tube body extending between the proximal end and the distal end;
   wherein a plurality of apertures are formed in the tube body, and wherein the apertures are arranged so as to define a density along the length of the tube body and the density of the apertures varies along the length of the tube body;
   disposing a medical device within the carrier tube to define a medical device assembly;
   disposing the medical device assembly within a packaging pouch; and
   exposing the medical device assembly to an alternative atmosphere.

10. The method of claim 9, wherein the medical device includes a catheter.

11. The method of claim 9, wherein the medical device includes a stent.

12. The method of claim 11, wherein the medical device includes a drug-eluting stent.

13. The method of claim 9, wherein exposing the medical device assembly to an alternative atmosphere includes exposing the medical device assembly to ethylene oxide.

14. The method of claim 9, wherein exposing the medical device assembly to an alternative atmosphere includes exposing the medical device assembly to the alternative atmosphere for less than about 12 hours to sterilize the medical device.

15. The method of claim 9, wherein exposing the medical device assembly to an alternative atmosphere includes exposing the medical device assembly to the alternative atmosphere for less than about 8 hours to sterilize the medical device.

16. The method of claim 9, wherein exposing the medical device assembly to an alternative atmosphere includes exposing the medical device assembly to the alternative atmosphere for less than about 4 hours to sterilize the medical device.

17. A time-efficient method for ethylene oxide sterilization of medical devices, the method comprising:

providing a carrier tube, wherein the carrier tube has a proximal end, a distal end, and a tube body extending between the proximal end and the distal end;

wherein a plurality of apertures are formed in the tube body, and wherein the apertures are arranged so as to define a density along the length of the tube body and the density of the apertures varies along the length of the tube body;

disposing a medical device within the carrier tube to define a medical device assembly;

disposing the medical device assembly within a packaging pouch; and exposing the medical device assembly to ethylene oxide far less than about 12 hours to sterilize the medical device assembly.

18. The method of claim 17, wherein exposing the medical device assembly to ethylene oxide includes exposing the medical device assembly to ethylene oxide for less than about 8 hours to sterilize the medical device assembly.

19. The method of claim 17, wherein exposing the medical device assembly to ethylene oxide includes exposing the medical device assembly to ethylene oxide for less than about 4 hours to sterilize the medical device assembly.

20. The method of claim 17, wherein exposing the medical device assembly to ethylene oxide for less than about 12 hours increases the shelf life of the medical device.

* * * * *

UNITED STATES PATENT AND TRADEMARK OFFICE
CERTIFICATE OF CORRECTION

PATENT NO.         : 8,235,209 B2
APPLICATION NO.    : 12/854607
DATED              : August 7, 2012
INVENTOR(S)        : James M. Peck et al.

It is certified that error appears in the above-identified patent and that said Letters Patent is hereby corrected as shown below:

Column 8
Line 10, after "define a density" and before "along the length", insert -- of the apertures --.
Line 36, after "define a density" and before "along the length", insert -- of the apertures --.

Column 9
Line 6, after "define a density" and before "along the length", insert -- of the apertures --.
Line 13, delete "far", and insert therefor -- for --.

Signed and Sealed this
Sixth Day of November, 2012

David J. Kappos
*Director of the United States Patent and Trademark Office*